United States Patent [19]
Rank et al.

[11] Patent Number: 5,234,426
[45] Date of Patent: Aug. 10, 1993

[54] HELICAL-TIPPED LESION LOCALIZATION NEEDLE DEVICE AND METHOD OF USING THE SAME

[75] Inventors: William R. Rank, Gretna; Ronald L. Nichols; Stephanie G. Schoenberger, both of New Orleans, all of La.

[73] Assignee: Research Corporation Technologies, Inc., Tucson, Ariz.

[21] Appl. No.: 988,616

[22] Filed: Dec. 10, 1992

Related U.S. Application Data

[62] Division of Ser. No. 679,464, Apr. 2, 1991, Pat. No. 5,197,482.

[51] Int. Cl.$^5$ .............................................. A61B 17/34
[52] U.S. Cl. ......................................... 606/1; 606/116; 606/185; 604/164
[58] Field of Search .......................... 606/1, 116, 185; 81/3.45; 604/164, 165; 128/698

[56] References Cited

U.S. PATENT DOCUMENTS

| | | | |
|---|---|---|---|
| 315,773 | 4/1885 | Haff | 81/3.45 |
| 1,062,458 | 5/1913 | Hainisch | 81/3.45 |
| 4,592,356 | 6/1986 | Gutierrez | 606/185 |
| 4,774,948 | 10/1988 | Markham | 606/185 |
| 5,059,197 | 10/1991 | Urie et al. | 606/116 |

*Primary Examiner*—Peter A. Aschenbrenner
*Attorney, Agent, or Firm*—Scully, Scott, Murphy & Presser

[57] ABSTRACT

A lesion localization and marking wire and needle assembly for marking non-palpable lesions within the body. A marking device having a helically wound coil of wire attached to an end of the shaft which is insertable into the body through a needle or cannula for rotatingly anchoring the marking device into a lesion or tumor is provided. The needle or cannula is inserted into the body with the marking device positioned therein so that when the cannula is positioned proximate to a lesion the shaft of the marker is rotated to advance the marker into the lesion to mark it for subsequent surgical procedures. A second helical wire may be provided on the shaft which cooperates with a wire guide device attached to the needle to enable the physician to determine the depth of the marking device as it anchors into the lesion. In particular, the device is provided for marking for biopsy lesions of the breast.

15 Claims, 4 Drawing Sheets

HELICAL-TIPPED LESION LOCALIZATION NEEDLE DEVICE AND METHOD OF USING THE SAME

This is a divisional of copending application Ser. No. 07/679,464, filed on Apr. 2, 1991, now U.S. Pat. No. 5,197,482.

BACKGROUND OF THE INVENTION

1. Field of the Invention

The present invention relates to lesion localization needles and devices, for use in localizing or marking non-palpable lesions and tumors within the body, and more particularly, the present invention relates to a needle assembly which includes a wire marker having a helically wound wire tip for rotatingly anchoring a marker to a lesion within a human breast.

Localization or marking of lesions within the body, such as non-palpable lesions discovered within the body, and devices such as needles and wires for marking these lesions, are well known in the art. The devices generally comprise a hypodermic needle or cannula which is inserted into the body under local anesthesia to a position adjacent and in contact with the lesion. The wire marker is then passed through the cannula and is anchored into the lesion so that the lesion is marked for subsequent surgical procedures such as excision or biopsy. After marking the lesion with the wire marker, the cannula is usually removed from the body, leaving the wire in place and extending from the body. However, these markers tend to dislodge and migrate during transport of the patient for the surgical biopsy procedure.

Increasingly, ultrasonic imaging is being used as a preferred ancillary or adjunctive imaging method to evaluate breast masses which may be associated with positive or negative mammographic findings. Currently available localization and marking devices image poorly, if at all, ultrasonically, making it difficult to accurately pinpoint the tip of the localization wire with respect to the lesion. Consequently, a subsequent surgical biopsy procedure may result in an inaccurate incision causing unnecessary tissue damage, and may necessitate a second surgical procedure to properly biopsy the lesion, causing the patient unnecessary pain, suffering, and expense.

2. Discussion of the Prior Art

In the prior art, several types of lesion localization devices and lesion markers are disclosed. Currently, the method of detecting and performing a biopsy on a non-palpable occult lesion within the body, such as non-palpable breast lesions, has been to radiologically or ultrasonically locate the lesion and to mark the lesion using a localization needle assembly, prior to a biopsy procedure. These needle assemblies generally comprise a hypodermic needle or cannula which is inserted into the body to an area adjacent to and in contact with the lesion. A marking wire is then inserted through the cannula into the lesion and anchored in place so that the cannula may be removed.

Ultrasonic imaging is increasingly being used as the preferred method of detection and evaluation of lesions and masses within the body due to its accuracy, and in view of the fact that the patient is not exposed to potentially harmful radiation for extended periods of time. The prior art marking devices generally image very poorly ultrasonically, as the tip of the previous marker shows up as a small, hard to locate dot or spot on the viewing screen. Depth perception is very limited, and consequently, accurate, reliable placement of the previous marking device is not guaranteed.

Nicholson, et al., U.S. Pat. No 4,616,656, discloses a probe wire and sheath assembly in which the wire has a J-type memory hook for marking lesions. The wire probe has a soft flexibility so that when it is enclosed within the sheath it has a straight configuration. The sheath, or needle, is inserted into the body, for instance into the breast of a female patient, and positioned proximate to a lesion. The wire probe is then pushed further into the lesion so that the memory hook is reformed and anchors itself within the lesion. The sheath is then removed leaving the hook embedded in the lesion as a marker.

A similar device is disclosed in Hawkins, Jr , U.S. Pat. No. 4,230,123. Hawkins, Jr. discloses a needle sheath assembly which consists of a small gauge needle in which a stylus or wire is positioned within a cannula. A shorter outer sheath is slidably located over the cannula which is removable after insertion of the needle into the patient's body. The wire has a J-type hook which is passed through the cannula to stabilize the tip of the cannula during biopsy.

Nicholson, et al. and Hawkins, Jr. are subject to several disadvantages which effect the accuracy and performance of the device. Devices such as those disclosed in these references image very poorly and are inconsistently visualized ultrasonically, and consequently may not be accurately placed. Furthermore, in procedures involving lesions of the breast, the breast is compressed during the mammographic localization procedure so that after the needle is in place and compression discontinued, the needle marker may inadvertently dislodge or migrate to a different position than that set during the localization procedure. The needle may also deflect away from the lesion, or if the strength and resiliency of the wire is less than that required to penetrate the lesion, the hook may not reform, allowing the marker to migrate or dislodge. This can result in damaging the tissues of the breast, as well as an inaccurate surgical incision during the biopsy procedure, usually requiring a second surgical procedure to properly biopsy the lesion, causing the patient unnecessary pain, suffering and expense. Devices of this type also generally require that the breast be stabilized during transport of the patient from the radiology section of a hospital to the surgical section for the biopsy procedure in order to prevent dislodgement of the marker.

Simon, U.S. Pat. No. 4,790,329, discloses a biopsy localization device having a sheath or cannula through which a barbed rod passes. The cannula is provided with an open side port through which the barb extends upon positioning within a lesion. In use, the barb is compressed within the lumen of the cannula and the pointed end of the rod extends from the cannula. As the device penetrates the patient's body, and into a lesion, the rod is rotated 180° so that the end of the barb may pass through the open side port of the cannula. The rod is then drawn back so that barb and cannula anchor into the lesion to prevent removal. While the device is relocatable, such as by drawing back the cannula to enclose the barbed rod after anchoring, it is apparent that some tissue damage will result due to the barb puncturing the tissue once it is anchored. In addition, the cannula remains in place while the lesion is marked by the barb, which results in excessive weight applied to the tissue. The entire device must be stabilized in order to prevent tearing of tissue and dislodgement of the marker. As related to breast lesions, as discussed above, compression of the breast during the procedure provides accurate anchoring of the barb; however, during transport of the patient, the additional weight of the cannula as well as the barbed rod will require stabilization of the breast to prevent migration and dislodgement of the device. A similar device, facing the same disadvantages, is disclosed in Hawkins, et al , U.S. Pat. No. 4,799,495.

An additional type of prior art lesion localization and biopsy device is commonly referred to as the "Nordenstrom Screw Diagnostic Instrument", which was developed by Bjorn Nordenstrom (Radiology, November 1975, Volume 117, Page 474). The Nordenstrom screw is generally a biopsy device and not a lesion localization and marking device. A cannula is provided which is inserted into the body, having a screw-tipped rod within the lumen of the cannula. When the cannula is positioned proximate a lesion, the rod is rotated to screw the tip into the lesion. The screw tip is integral with the rod itself, and is a finely machined device in which the screw threads define grooves which taper to the tip of the device. After the screw tip is rotated into the lesion, the cannula is then rotated in an opposite direction using slight forward pressure to a position over the screw threads. Tissue from the lesion is captured in the grooves of the screw tip and the entire device is withdrawn so that the tissue may be examined. The Nordenstrom screw device, as stated above, is not a marking device, but instead allows the physician to immediately biopsy the lesion in question.

An additional marking device using a screw tip is disclosed in Hawkins, et al., U.S. Pat. No. 4,799,495. In this device, the cannula may be provided with a tapering screw tip to anchor the cannula in the tissue while the needle marker penetrates the lesion. The cannula and wire are used to mark the lesion, and Hawkins et al. also discloses the use of the cannula alone for marking the lesion. Furthermore, Hawkins et al. discusses a helical screw needle marker, similar to the Nordenstrom screw device, which may be inserted through the cannula to mark the lesion. However, the tapering screw tip of Hawkins et al is a finely machined device which is quite expensive to manufacture, and which also is subject to the disadvantage that the tapered end may result in the loosening or "backing off" of the screw tip which will dislodge the marker during transport of the patient, or upon discontinuation of compression of the breast during the marking procedure. Furthermore, the precise machining of the tip of this device, and in particular a hollow screw-tipped cannula, would be a difficult and very expensive procedure from a manufacturing standpoint, and would necessitate that the device be reusable due to these cost considerations. In view of this, and in light of current health risks and concerns for patient safety as related to blood products and invasive surgical procedures, sterilization procedures would be required prior to and after each use, thereby making the procedure more elaborate and expensive then normally necessary.

The novel, disposable lesion localization and marking device of the present invention obviates the problems associated with the prior art lesion localization devices by providing an inexpensive, simple to manufacture lesion marking device having a helically wound marking wire attached to a wire shaft which passes through a hypodermic needle comprising a cannula. The helically wound marking wire extends concentrically outward from the shaft and maintains a substantially uniform diameter so that once the wire is rotated or screwed into a lesion, it remains anchored in the tissue without the possibility of backing off and dislodging.

In a preferred embodiment, a second helically wound wire is provided on the shaft remote from the first helically wound wire at the tip which, in conjunction with a wire guide provided on a gripping knob of the cannula, assists in the forward advancement of the shaft so that excessive forward pressure is not required, and the second helix also acts as a depth guide to provide an accurate indication of the depth to which the first helix is embedded in a lesion. The helically wound wires are secured to the shaft by means such as soldering, or may be wound as part of the shaft itself, so that the entire device is simple to manufacture and relatively inexpensive, thereby making the device disposable following the biopsy procedure.

SUMMARY OF THE INVENTION

The present invention eliminates or substantially ameliorates the disadvantages encountered in the prior art through the provision of a lesion localization and marking device having a helically wound wire tip attached to a shaft which is inserted within the lumen of a cannula into the body and then rotated into a lesion to anchor the marker within the lesion tissue. The device is simple to manufacture and inexpensive thereby making it a disposable unit, which may be packaged in a sterile packaging unit for one time use.

The lesion localization and marking device of the present invention consists of a marker having a shaft constructed of stainless steel or other biocompatable material which has secured to its distal end, or formed integrally thereon, a stainless steel wire which is helically wound about the end of the shaft. The helically wound wire extends outwardly in a concentric manner from the end of the shaft and overhangs the shaft a predetermined distance. The end of the helix is sharpened to facilitate insertion into a lesion within the body. The helical wire is secured to the shaft by conventional means such as soldering.

The marking device, when used in conjuction with the needle assembly of the present invention, may be provided with a second helically wound wire which is secured to the shaft of the marker remote from the end having the first helically wound wire. The second helically wound wire is secured to the shaft by soldering, or integrally formed as part of the shaft, and is dimensioned to have the same number of turns per centimeter as the first helically wound wire, thus having the same pitch or angle for each turn of coil. The marking device is positioned within a hypodermic needle or cannula which essentially comprises a stainless steel tube having a cutting edge at one end and a thermoplastic gripping knob at its other end. The gripping knob has a hole bored through the center which preferably aligns with the lumen of the cannula, and a second hole is bored through the knob parallel to the first hole and offset from the center of the lumen. Through the second hole is positioned a wire guide which is bent perpendicular to the hole and placed to partially cover the first hole, leaving an opening which is substantially equal to the diameter of the shaft of the wire marker plus the diameter of the wire which forms the helix.

In use, the needle assembly is inserted into the body, such as into the breast of a female patient, until the tip of the cannula is proximate to a lesion which has been discovered during a mammogramphic or ultrasonic imaging procedure. The marking device is positioned within the cannula so that the sharpened tip of the first helical wire is adjacent to the cutting edge of the cannula, and the second helical wire is positioned a predetermined distance such that the end of the second helical wire closest to the first helical wire is adjacent to and engages the wire guide of the thermoplastic knob of the cannula. As the marking device is rotated, the second helical wire is guided along the wire guide so as to stabilize the shaft while drawing the marker into the cannula due to the interaction of the second helix and the wire guide during rotation, and the first helical wire is rotated into the lesion. The wire guide assists the forward advancement of the marker during rotation.

The length of the second helical wire is identical to the length of the first helical wire from the end of the shaft to the sharpened tip, and both helical wires have an identical number of turns per centimeter. As the first helical wire is embedded into the lesion, the physician can accurately gauge the depth to which the first wire enters the lesion by the distance the second helical wire extends outwardly from the gripping knob of the cannula. When the second helical wire is fully rotated within the cannula the physician will know that the first wire is fully extended outside the cannula and is in position with respect to the lesion. The cannula is then removed from the body leaving the marking device in place.

As ultrasonic imaging is increasingly being used as the preferred method of evaluation of breast lesions in localization procedures, it is very important the the marker used in the localization procedure provide consistent visualization and clean imaging with a recognizable acoustic pattern. Prior art markers do not provide adequate ultrasonic imaging and consequently do not contribute to accurate localization of a lesion The present invention, however, due to the helical tip, provides excellent imaging characteristics compared to prior art markers, such that each turn of the helix images distinctly, as opposed to the single spot or dot appearing from the prior art markers. As a result, the present marker provides an unambiguous ultrasonic image allowing for accurate marking of the discovered lesion under the same conditions as mammography, thus reducing the patient's exposure to X-rays as well as decreasing the number of repositions required to accurately mark the lesion.

Accordingly, it is a primary object of the present invention to provide an inexpensive, simple to manufacture, and disposable marking device for localizing lesions within the body, particularly breast lesions.

It is a further object of the present invention to provide a lesion localization device which substantially eliminates the possibility of dislodgement or migration of the needle marker after placement.

It is yet another object of the present invention to provide a lesion localization device which may be relocated or repositioned within the body which minimizes or substantially eliminates damage to tissue during repositioning.

A still further object of the present invention is to provide a lesion localization device which presents an unambiguous echo when exposed to ultrasonic sound waves, allowing placement of the device to be carried out without the need for the use of X-ray imaging.

A still further object of the present invention is to provide a lesion localization device in which the depth to which the lesion marker is placed with respect to a lesion is readily and accurately determined.

A still further object of the present invention is to provide a marking device for localizing non-palpable breast lesions which can be firmly anchored in the lesion and will not be dislodged regardless of the positioning or stability of the breast tissue.

Yet another object of the present invention is to provide an efficient and accurate method for marking non-palpable lesions within the body, particularly within the breast.

BRIEF DESCRIPTION OF THE DRAWINGS

The foregoing objects and other features of the invention will become more readily apparent and may be understood by referring to the following detailed description of an illustrative embodiment of the lesion localization and marking device having a helically wound wire tip, taken in conjunction with the accompanying drawings; in which:

FIG. 3a illustrates an elevational end view of the gripping knob of the hypodermic needle of FIG. 2 along lines 3a–3a;

DETAILED DESCRIPTION OF THE PREFERRED EMBODIMENTS

Figure 1:
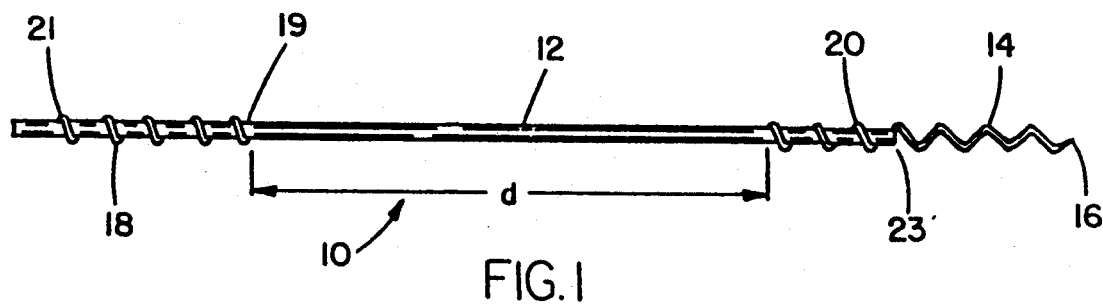
FIG. 1 illustrates a side elevational view of a marking device pursuant to the present invention.

Referring now in specific detail to the drawings, in which identical reference numberals identify similar or identical elements throughout the several views, FIG. 1 shows marking device 10 according to the present invention. Marking device 10 is constructed of a biocompatable material, and is preferably constructed of stainless steel, although many metal alloys such as aluminum alloy, titanium alloy, ferrous alloy, and the like, as well as materials such as plastic and ceramic, may be employed. Marking device 10 essentially consists of a shaft 12 which is preferably type 18-8 stainless steel having a thickness of between 0.011 and 0.20 inches diameter, and is preferably 0.016 inches diameter. Marking device 10 is provided at one end with helical marking wire 14 which is helically wound about the end of shaft 12 and secured to the shaft as illustrated at 20. Preferably, helical marking wire 14 is constructed of the same material as shaft 12, and is secured to the shaft by soldering, preferably of a 98% tin and 2% silver solder. Helical marking wire 14 is wound about shaft 12 and extends outwardly away from the shaft to terminate in a sharpened tip 16. The diameter of the coil formed by helix 14 remains constant along its length Helix 14 extends from the end of shaft 12 a distance of between 0.5 centimeters and 2 centimeters, and preferably extends 1 centimeter from the end of shaft 12. The pitch of the coil is determined by the number of turns per centimeter, which along with the length of helix 14, is dependent upon the application for which the marker is to be used. Different tissues within the body have different degrees of strength and resiliency, some requiring more force to anchor the marker 10 in place, and thus some tissues require a device having more turns per centimeter than other tissues. Accordingly, helix 14 generally is provided with between 6 and 15 turns per centimeter, and preferably it is provided with 8 turns per centimeter for marking breast lesions.

Separated a distance "d" along shaft 12 from helical marking wire 14 is helical guide wire 18 which is also wound about shaft 12. Helix 18 is constructed of the same material as helix 14 and shaft 12, and helical wires 14 and 18 are the same gauge wire, preferably having a diameter of between 0.009 and 0.015 inches (0.02 and 0 04 cm). The preferred diameter for helical wires 14 and 18 is 0.011 inches (0.027 cm) for marking breast lesions. Helix 18 is secured to shaft 12 in a manner similar to helix 14. Helix is of the same length as the length that helix 14 extends from the end of shaft 12 to sharpened tip 16, and also has the identical amount of turns per centimeter as helix 14, and thus the same pitch to the coil formed by helix 18.

Distance "d" is dependent upon the length of the hypodermic needle or cannula with which marking device 10 is to be used. This will be described in greater detail below.

Figure 2:
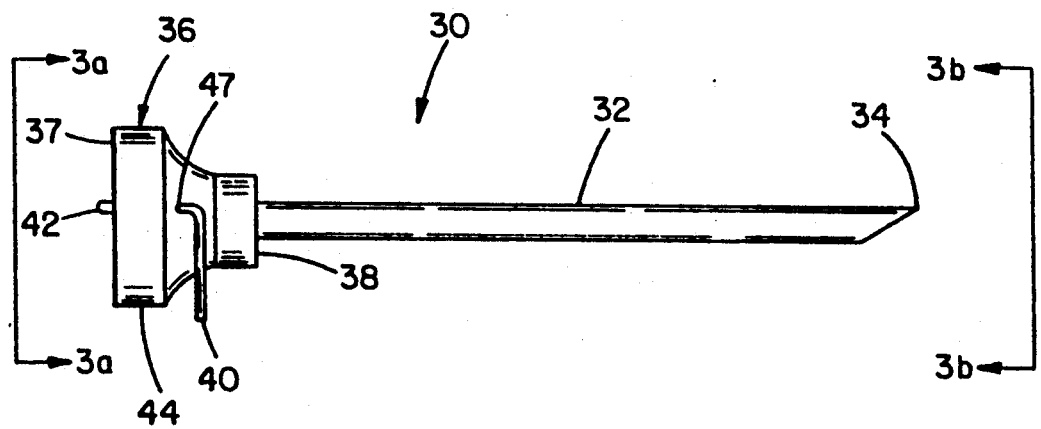
FIG. 2 illustrates a side elevational view of a hypodermic needle or cannula pursuant to the present invention.
Figure 3B:
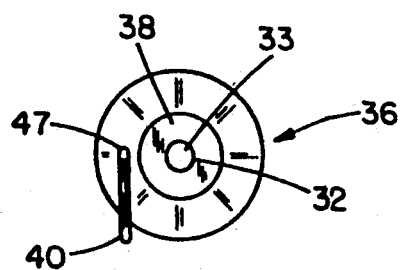
FIG. 3b illustrates an elevational end view of the cannula of the hypodermic needle of FIG. 2 along lines 3b–3b.

As can be seen in FIG. 2, hypodermic needle 30 comprises a cannula 32 having a sharpened cutting tip 34 and a gripping knob 36. Cannula 32, like marking device 10, is constructed of biocompatable material, and is preferably stainless steel. In a preferred embodiment, the cannula is 18-gauge thin wall stainless steel type 504, and has a length from tip 34 to knob end 36 of between 3 and 15 centimeters, depending upon the type and location of the lesion to be marked. Knob 36 is preferably constructed of thermoplastic material such as nylon and is secured to cannula 32 at end 38 by conventional means such as epoxy, adhesives, and the like. Knob 36 may have a ridged gripping surface 44 which aids the physician in handling the needle 30. Cannula 32 is of course hollow and defines a lumen 33, as best seen in FIG. 3B.

Figure 3A:
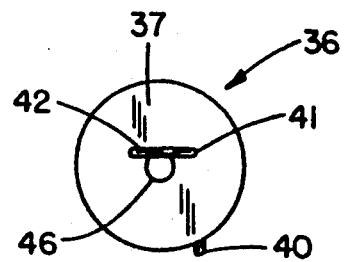

Gripping knob 36 has a hole 46 bored through the knob, which in the preferred embodiment aligns with lumen 33 of cannula 32 so that the cannula can extend through the hole to face 37 of knob 36. In addition to hole 46, a second hole 47 is bored through knob 36, which is offset and parallel to hole 46. A wire guide 40 passes through hole 47 and may be secured within the hole by conventional means such as epoxy, adhesives, and the like. Wire guide 40 passes through hole 47 and is bent at 41 along face 37 of knob 36 to form guide bar 42. Wire guide 40 may also loosely and pivotably rest within hole 47 so that guide bar 42 may be moved into and out of engagement with shaft 12 of marker 10. As seen in FIG. 3a, guide bar 42 partially covers hole 46 in knob 36 so as to reduce the opening of hole 46. The reason for this will be explained in greater detail below.

Figure 4:
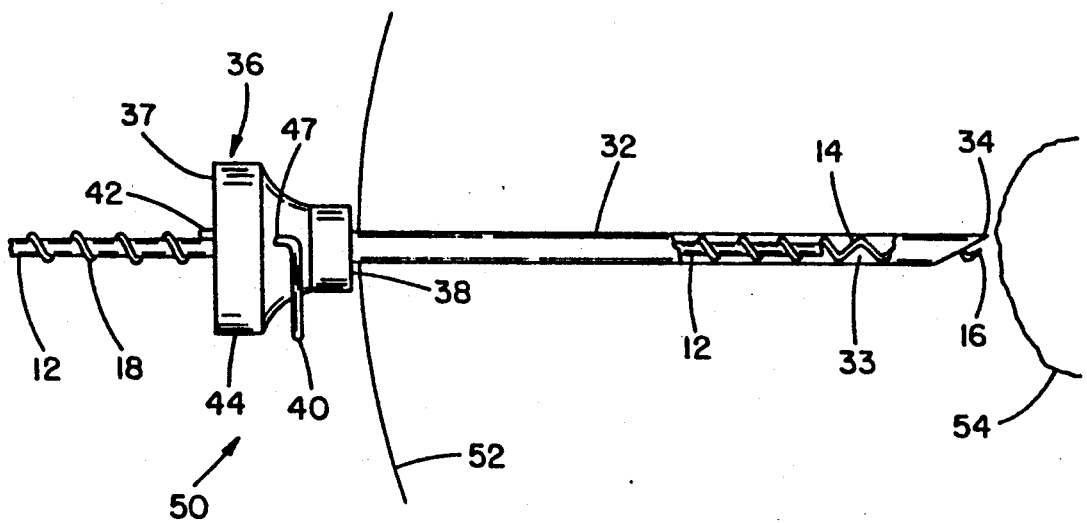
FIG. 4 illustrates a perspective, partially sectional view of the lesion localization needle assembly pursuant to the present invention after insertion into the body but prior to marking a lesion.
Figure 5:
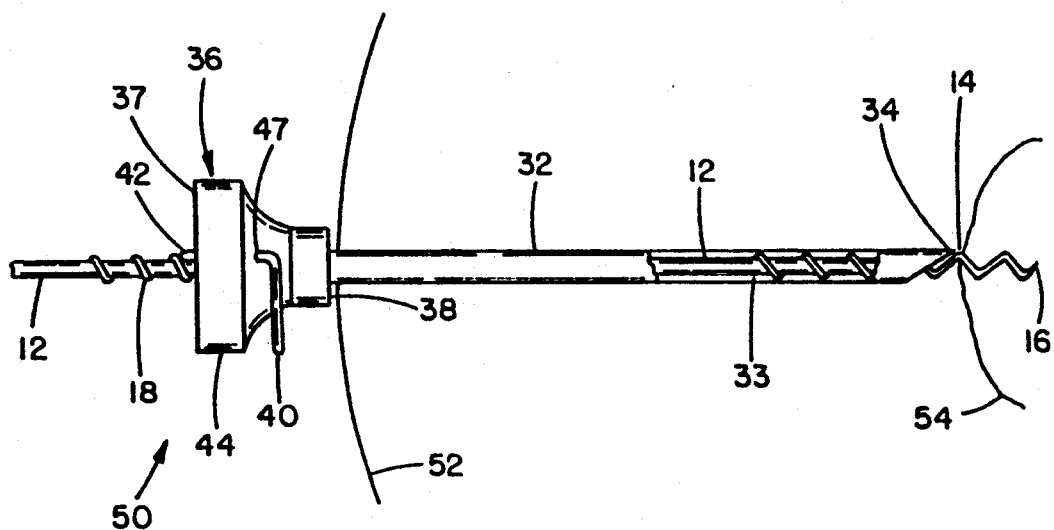
FIG. 5 illustrates a perspective, partially sectional view of the needle assembly of FIG. 4 during rotation of the marking device within the cannula and into a lesion.
Figure 6:
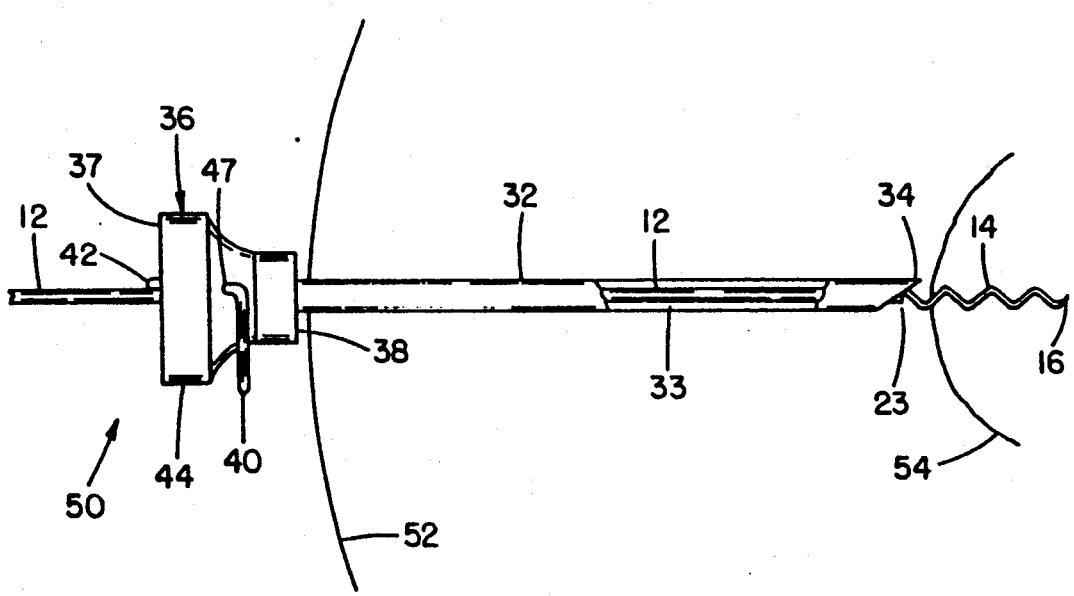
FIG. 6 illustrates the needle assembly of FIG. 4 after rotation of the marking device into the cannula with the wire marker being fully embedded within a lesion.

FIGS. 4, 5 and 6 show needle and marker assembly 50 in various positions during use of assembly 50 in marking a lesion within the body. Assembly 50 comprises marking device 10 as shown in FIG. 1 positioned within the lumen 33 of needle 30 as shown in FIG. 2. The location of the lesion within the body, such as non-palpable lesions found in the breast or organs deep within the body, is determined radiologically or ultrasonically in a non-invasive procedure. In order to biopsy the lesion or remove it, the surgeon must have an accurate location of the lesion prior to performing the surgical procedure to minimize damage to tissue. The accuracy of the location of the marker will obviate any need for additional incisions, as well as avoid unnecessary tissue removal, which benefits the patient both physically and cosmetically. The use of a marking device such as in the present invention is illustrated in FIGS. 4, 5 and 6.

As seen in FIG. 4, the needle and marker assembly 50 is inserted into the body through the skin surface 52 until cutting tip 34 of cannula 32 is positioned proximate a lesion or tumor 54. Marking device 10 is positioned within needle 30 such that sharpened tip 16 of helical marking wire 14 is positioned adjacent to cutting tip 34 of needle 30. The length of needle 30, as well as the length of shaft 12 and distance "d" between marking wire 14 and guide wire 18 is determined by the depth or distance lesion 54 is from the surface of the skin 52. Distance "d" is determined such that when marking device 10 is within the lumen 33 of needle 30, forward end 19 of helical guide wire 18 engages and rests against guide bar 42, resulting in sharpened tip 16 being adjacent to cutting tip 34.

Turning now to FIG. 5, after cutting tip 34 is positioned proximate to lesion 54, marking device 10 is rotated about shaft 12 to advance helical marking wire 14 into lesion 54. Sharpened tip 16 enters lesion 54 and the rotation about shaft 12 further advances marking wire 14 into the lesion to firmly anchor it in place. The depth to which helical marking wire 14 enters lesion 54 is determined by the distance helical guide wire 18 travels through hole 46 into cannula 32. As shaft 12 is rotated, guide bar 42 of wire guide 40 engages the shaft and helix 18 at end 19 of helix 18 and guides shaft 12 while allowing helical guide wire 18 to rotate into hole 46 in a screw-like fashion. Guide bar 42 is positioned between the individual coils of helical guide wire 18 to prevent slipping or pulling on the shaft. Wire guide 40 may be secured in hole 47 or may be pivotably secured so that guide bar 42 may rotated away from shaft 12 to disengage guide bar 42 from helix 18.

When helical marking wire 14 is embedded and anchored in lesion 54, that is when the end 23 of shaft 12 is proximate to the lesion 54, the rotation is ceased. This is best seen in FIG. 6 The surgeon may determine when marking wire 14 is in its desired position with respect to lesion 54 when guide wire 18 completely disappears into knob 36 past guide bar 42. The trailing end 21 of guide wire 18 is the same distance from the end 23 of shaft 20 as the distance between forward end 19 of guide wire 18 and sharpened tip 16 of marking wire 14. When the surgeon determines that the marking wire 14 in proper position, such as when it is completely embedded in the lesion, as evidenced by trailing end 21 of helix 18 turning into knob 36, the surgeon may then remove needle 30 from the body leaving marking device 10 firmly embedded in the lesion. Alternatively, when it is determined that the helix 14 is in a desired position with respect to lesion 54 without helix 18 being completely within cannula 32, such as when a lesion is located proximate the chest wall as determined by ultrasonic imaging, wire guide 40 may be pivoted to rotate guide bar 42 away from helix 18 to allow for removal of needle 30 without disturbing the position of helix 14. Marking device 10 remains firmly anchored due to the concentric nature of the coils of marking wire 14 and eliminates the possibility of inadvertent dislodgement due to relaxation of the tissues of the breast upon discontinuing the compression placed on the breast during the procedure.

Figure 7:
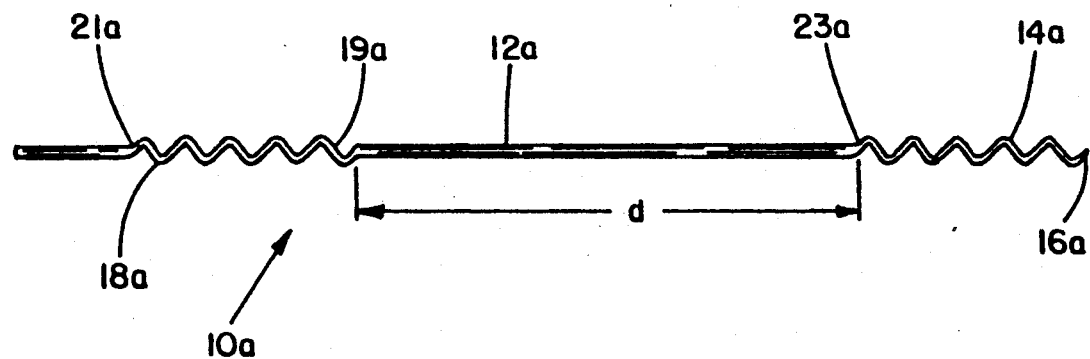
FIG. 7 illustrates a side elevational view of an alternate embodiment of a marking device pursuant to the present invention.

FIG. 7 illustrates an alternate embodiment of the present invention showing marking device 10a, in which helix 14a and helix 18a are integrally wound as part of shaft 12a. FIG. 7 is identical to FIG. 1 in operation and function except that additional helical wires are not needed, since marking device 10a is of unitary construction in that shaft 12a and helixes 14a and 18a are constructed as a single unit. In a further embodiment, helix 14 and helix 18 may be joined so that the entire shaft 12 is in a helical coil.

Figure 8:
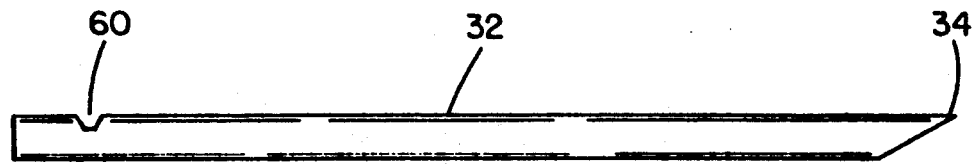
FIG. 8 illustrates a side elevational view of an alternate embodiment of a needle or cannula pursuant to the present invention.

In a further embodiment, cannula 32 may be provided with a notched portion 60, and knob 36 may be eliminated, as seen in FIG. 8. In this case, notch 60 engages helix 18, or alternately helix 14, dependent upon location of notch 60. Notch 60 will then guide marking device 10 in the same manner as wire guide 40 and guide bar 42.

While the invention has been particularly shown and described with reference to the preferred embodiments, it will be understood by those skilled in the art the various changes in form and detail may be made therein without departing from the spirit and scope of the invention. Accordingly, modifications and/or changes such as removing guide wire 18 or providing a longer or shorter marking wire, as well as increasing or decreasing the pitch of the coils as related to the number turns per centimeter, may be provided as desired, and are considered to be within the scope of the invention.

What is claimed is:

1. A needle assembly for localization of lesions within the body, comprising:
    a needle cannula, said cannula having a cutting edge at a first end; and
    a marking device positioned within said cannula and including a shaft, said marking device further including a wire helically wound at one end of said shaft and extending beyond said end a predetermined distance in a helical coil, and having a sharpened tip, said marking device being axially slidable and rotatable within said cannula.

2. A needle assembly according to claim 1, wherein said wire is wound about and secured to said shaft.

3. A needle assembly according to claim 1, wherein said cannula and said marking device are constructed of biocompatable material.

4. A needle assembly according to claim 3, wherein said cannula and said marking device are constructed of stainless steel.

5. A needle assembly according to claim 3, wherein said cannula and said marking device are constructed of a metal alloy.

6. A needle assembly according to claim 1, wherein said helical coil of said wire has a constant diameter along its length.

7. A marking device for marking lesions within the body comprising:
    a shaft; and
    a helically coiled wire wound about and secured to an end of said wire shaft,
    wherein said helically coiled wire extends concentrically outwardly from said end of said shaft and away from said shaft, said helically coiled wire having a sharpened end remote from said shaft.

8. A marking device according to claim 7, wherein said coiled wire is soldered to said shaft.

9. A marking device according to claim 7, wherein said coiled wire is wound about said shaft between 6 and 15 turns per centimeter.

10. A marking device according to claim 9, wherein said coiled wire is wound about said shaft 8 turns per centimeter.

11. A marking device according to claim 7, wherein said coiled wire has a diameter less than or equal to the diameter of said shaft.

12. A marking device for marking lesions within the body, comprising:
    a shaft;
    a first helically coiled wire secured to and wound about a first end of said shaft, said first wire extending concentrically outwardly from said first end and away from said shaft a predetermined length and terminating in a sharpened tip; and
    a second helically coiled wire secured to and wound about said shaft a distance from said first helically coiled wire, said second wire having a length equal to said predetermined length that said first wire extends from said shaft;
    wherein said first and second helically coiled wires are wound an equal number of turns per centimeter.

13. A marking device according to claim 12, wherein said first and second coiled wires are wound between 6 and 15 turns per centimeter 14. A marking device according to claim 13, wherein said first and second coiled wires are wound 8 turns per centimeter.

15. A marking device according to claim 14, wherein said length of said second coiled wire and said predetermined length of said first coiled wire is 1 centimeter.

* * * * *

UNITED STATES PATENT AND TRADEMARK OFFICE
CERTIFICATE OF CORRECTION

PATENT NO. : 5,234,426
DATED : August 10, 1993
INVENTOR(S) : William R. Rank, et al.

It is certified that error appears in the above-indentified patent and that said Letters Patent is hereby corrected as shown below:

```
Column 2, line 17:     "Jr,"   should read --Jr.,--
Column 3, line 45:     after "et al" insert --.--
Column 5, line 40:     after "lesion" insert --.--
Column 7, line 10:     after "length" insert --.--
Column 7, lines 30-31: "0 04 cm"  should read
--0.04 cm--
Column 7, line 34:     after "Helix" insert --18--
Column 8, line 60:     after "6" insert --.--
```

Signed and Sealed this

Nineteenth Day of July, 1994

Attest:

BRUCE LEHMAN

*Attesting Officer*         Commissioner of Patents and Trademarks